(12) United States Patent
Zhou et al.

(10) Patent No.: US 12,196,755 B2
(45) Date of Patent: Jan. 14, 2025

(54) IMMUNOASSAY PLATFORM FOR THE SEROLOGICAL DISCRIMINATION OF CLOSELY RELATED VIRUSES

(71) Applicant: Zymeron Corporation, Durham, NC (US)

(72) Inventors: Yan Zhou, Durham, NC (US); Zhiguo Zhou, Durham, NC (US); Qian Li, Durham, NC (US)

(73) Assignee: Zymeron Corporation, Durham, NC (US)

( * ) Notice: Subject to any disclaimer, the term of this patent is extended or adjusted under 35 U.S.C. 154(b) by 240 days.

(21) Appl. No.: 17/541,065

(22) Filed: Dec. 2, 2021

(65) Prior Publication Data

US 2023/0176072 A1 Jun. 8, 2023

(51) Int. Cl.
*G01N 33/569* (2006.01)
*G01N 33/533* (2006.01)
(Continued)

(52) U.S. Cl.
CPC ..... *G01N 33/56983* (2013.01); *G01N 33/533* (2013.01); *G01N 33/54306* (2013.01);
(Continued)

(58) Field of Classification Search
CPC ........... G01N 33/56983; G01N 33/533; G01N 33/54306; G01N 33/6854; G01N 33/6887;
(Continued)

(56) References Cited

U.S. PATENT DOCUMENTS 7,351,547 B2    4/2008    Wong et al.
7,384,785 B2    6/2008    Wong et al.
(Continued)

FOREIGN PATENT DOCUMENTS

WO    2016022071 A1    2/2016

OTHER PUBLICATIONS

Tyson J, Tsai W-Y, Tsai J-J, Mässgård L, Stramer SL, Lehrer AT, et al. (2019) A high-throughput and multiplex microsphere immunoassay based on non-structural protein 1 can discriminate three flavivirus infections. PLoS Negl Trop Dis 13(8): e0007649. https://doi.org/10.1371/journal.pntd.0007649 (Year: 2019).*
(Continued)

*Primary Examiner* — Gregory S Emch
*Assistant Examiner* — Mckenzie A Dunn
(74) *Attorney, Agent, or Firm* — Michael Best & Friedrich LLP

(57) ABSTRACT

An immunoassay platform and methodology are described for discriminatively detecting target microorganism antibodies to a target antigen in a biological sample derived from a host animal, from among antibodies of cross-reactively-related microorganism(s) potentially present in the biological sample, by use of contemporaneous assays conducted with and without blocking antibodies exogenous to the host animal. Attenuation of detection reagent signal between the contemporaneous assays may be used to determine a target antigen previously infected or non-infected status of the host animal. An assay system is described, including: a single-use cartridge containing test strips constituted to perform the immunoassay; an integrated sample collection and processing device engageable with the single-use cartridge for delivery of sample thereto, and for operatively initiating immunoassay performance in the single-use cartridge; and a
(Continued)

portable immunoassay reader for reading immunoassay output signals from the test strips of the single-use cartridge.

20 Claims, 1 Drawing Sheet

(51) Int. Cl.
*G01N 33/543* (2006.01)
*G01N 33/68* (2006.01)

(52) U.S. Cl.
CPC ..... *G01N 33/6854* (2013.01); *G01N 33/6887* (2013.01); *G01N 33/54388* (2021.08); *G01N 2333/185* (2013.01); *G01N 2469/20* (2013.01); *G01N 2470/12* (2021.08)

(58) Field of Classification Search
CPC ......... G01N 33/54388; G01N 2470/12; G01N 2333/185; G01N 2469/20
See application file for complete search history.

(56) References Cited

U.S. PATENT DOCUMENTS

| | | | |
|---|---|---|---|
| 7,932,099 B2* | 4/2011 | Egan | C12Q 1/701 435/7.1 |
| 9,650,422 B2 | 5/2017 | Chang et al. | |
| 10,060,924 B2 | 8/2018 | Ulbert et al. | |
| 10,338,061 B2 | 7/2019 | Kwon et al. | |
| 10,987,669 B2 | 4/2021 | Xie et al. | |
| 2009/0320623 A1* | 12/2009 | Matallana-Kielmann | G01N 33/54388 73/864.91 |
| 2018/0038852 A1* | 2/2018 | Manuguerra | G02B 27/4272 |
| 2019/0359694 A1 | 11/2019 | Lipkin et al. | |
| 2021/0349104 A1* | 11/2021 | Wohlstadter | G01N 33/56983 |

OTHER PUBLICATIONS

Al Qaraghuli, Mohammed M et al. "Antibody-protein binding and conformational changes: identifying allosteric signalling pathways to engineer a better effector response." Scientific reports vol. 10,1 13696. Aug. 13, 2020, doi:10.1038/s41598-020-70680-0 (Year: 2020).*

Rabia, Lilia A et al. "Understanding and overcoming trade-offs between antibody affinity, specificity, stability and solubility." Biochemical engineering journal vol. 137 (2018): 365-374. doi:10.1016/j.bej.2018.06.003 (Year: 2018).*

Poosarla, Venkata Giridhar et al. "Computational de novo design of antibodies binding to a peptide with high affinity." Biotechnology and bioengineering vol. 114,6 (2017): 1331-1342. doi:10.1002/bit.26244 (Year: 2017).*

Lloyd, C et al. "Modelling the human immune response: performance of a 1011 human antibody repertoire against a broad panel of therapeutically relevant antigens." Protein engineering, design & selection : PEDS vol. 22,3 (2009): 159-68. doi:10.1093/protein/gzn058 (Year: 2009).*

Khan, Tarique, and Dinakar M Salunke. "Adjustable locks and flexible keys: plasticity of epitope-paratope interactions in germline antibodies." Journal of immunology (Baltimore, Md. : 1950) vol. 192,11 (2014): 5398-405. doi:10.4049/jimmunol.1302143 (Year: 2014).*

Goel, Manisha et al. "Plasticity within the antigen-combining site may manifest as molecular mimicry in the humoral immune response." Journal of immunology (Baltimore, Md. : 1950) vol. 173,12 (2004): 7358-67. doi:10.4049/jimmunol.173.12.7358 (Year: 2004).*

Edwards, Bryan M et al. "The remarkable flexibility of the human antibody repertoire; isolation of over one thousand different antibodies to a single protein, BLyS." Journal of molecular biology vol. 334, 1 (2003): 103-18. doi:10.1016/j.jmb.2003.09.054 (Year: 2003).*

Sadeghi, Poorya et al. "Lateral flow assays (LFA) as an alternative medical diagnosis method for detection of virus species: The intertwine of nanotechnology with sensing strategies." Trends in analytical chemistry : TRAC vol. 145 (2021): 116460. doi: 10.1016/j.trac.2021.116460 (Year: 2021).*

Balmaseda, A., et al., "Antibody-based assay discriminates Zika virus infection from other flaviviruses", PNAS, 2017, pp. 8384-8389, vol. 114, No. 31.

Rockstroh, A., et al., "Recombinant Envelope-Proteins with Mutations in the Conserved Fusion Loo; Allow Specific Serological Diagnosis of Dengue-Infections", PLOS, 2015, Page(s) https://doi.org/10.1371/journal.pntd.ooo4218.

International Searching Authority. International Preliminary Report on Patentability for Application No. PCT/US2022/080801, dated May 2, 2024 (8 pages).

International Searching Authority. International Search Report and Written Opinion for Application No. PCT/US2022/080801, dated Mar. 8, 2023 (10 pages).

* cited by examiner

IMMUNOASSAY PLATFORM FOR THE SEROLOGICAL DISCRIMINATION OF CLOSELY RELATED VIRUSES

GOVERNMENT RIGHTS IN INVENTION

The invention hereof was made in part with Government support under U.S. Department of Defense Contract W81XWH20P0035. The government has certain rights in the invention.

FIELD

The present disclosure relates to an immunoassay platform and methodology for discriminating antibodies of closely related viruses having high levels of cross-reactivity between each other in biological samples in which they may be contemporaneously present, and which when present render it difficult to identify specific virus infection.

DESCRIPTION OF THE RELATED ART

A major challenge of serological assays is to discriminate viral infection of a specific virus from among closely related viruses that exhibit high levels of cross-reactivity between each other, thereby making it difficult to study the epidemiology of such viruses and their interaction when such viruses are contemporaneously circulated.

Immunoassays have been widely used for serological testing for diagnosing virus infection, but despite being fast, simple, and cost-effective in character, face challenges in providing high sensitivity, high specificity serological assays of target viruses in instances of high levels of cross-reactivity from closely related viruses that may have similar structures, co-circulate in the same areas, and cause similar symptoms.

The Flavivirus family is illustrative. Flavivirus is a genus of positive-strand RNA viruses that include Dengue virus (DENV), Zika virus, Yellow Fever virus, West Nile virus, Japanese Encephalitis virus, and several other viruses that may cause encephalitis. All members of the genus Flavivirus are closely related and share significant amino acid sequence identity, which results in serological cross-reactivity. Conventional immunoassays (e.g., enzyme-linked immunosorbent assays (ELISAs) and rapid diagnostic tests (RDTs)) using traditional viral antigens that include structurally conserved epitopes to detect antibodies have been found to poorly differentiate among flavivirus infections.

For example, one study that evaluated three ELISA commercial tests for DENV IgG and IgM (Focus Dengue Virus IgG DxSelect™ and DengueVirus IgM Capture DxSelect™ (FOCUS DIAGNOSTICS, Cypress, CA, USA), Euroimmun Anti-Dengue Virus ELISA IgG and IgM (EUROIMMUN AG, Luebeck, Germany) and Panbio Dengue IgG and IgM capture ELISA (Panbio, Brisbane, Australia)) indicated that all three tests showed cross reactivity with anti-Zika IgG and IgM at some level. Specifically, DENV IgG positivity reached 100% for all three tests when testing serum samples from a total of 61 patients with non-Dengue confirmed Zika virus infection (Felix A. C., Souza N. C. S., Figueiredo W. M., Costa A. A., Inenami M., da Silva R. M. G., Levi J. E., Pannuti C. S., Romano C. M., Cross reactivity of commercial anti-dengue immunoassays in patients with acute Zika virus infection. J. Med. Virol. 2017 August; 89(8):1477-1479).

Currently, efforts have been directed toward identifying target virus-specific epitopes and generating recombinant mutant antigens or monoclonal antibodies that show high specificity, so that an accurate determination of viral serostatus can be made. For example, in one recent study, the researchers developed recombinant E protein antigens with mutants in the conserved fusion loop domain that successfully differentiated human Dengue IgG from other flaviviruses (Yellow Fever virus, West Nile virus and Tick-borne encephalitis virus) in an ELISA assay (Ulbert S., Chabierski, S., Diamond, M., Fremont, D., U.S. Patent Application Publication 20170089897, Mar. 30, 2017). However, the development of such mutant antigens requires a special strategy including 1) identification of epitopes related to a specific target virus; 2) careful design and production of recombinant antigens; and 3) testing of multiple recombinant antigens to find the most suitable one that can differentiate the target virus from others. The entire process of developing such recombinant antigens is time-consuming, complex, and costly.

In summary, immunoassay methods such as enzyme-linked immunosorbent assay (ELISA) and lateral flow assay (LFA) use traditional viral antigens, and have been found to poorly differentiate closely related viruses exhibiting high cross-reactivity due to the significant level of structurally conserved epitopes on the viral antigens. The use of modified antigens with mutations on the conserved epitopes has potential for improved specificity but will also markedly increase the cost and complexity of the assay.

As a consequence, the art continues to seek improvements in assay platforms and techniques for discriminating closely related and highly cross-reactive viruses.

SUMMARY

The present disclosure relates to an immunoassay platform and methodology for discriminating closely related viruses exhibiting high levels of cross-reactivity between each other.

In one aspect, the disclosure relates to an immunoassay for discriminatively detecting target microorganism antibodies in a human sample, from among antibodies of cross-reactively-related microorganism(s) potentially present in the human sample, the immunoassay comprising: (a) immobilizing target microorganism antigen on each of first and second immunoassay substrates; (b) introducing corresponding amounts of the human sample to each of the first and second immunoassay substrates on which the target microorganism antigen has been immobilized; (c) introducing non-human antibodies against target microorganism antigen to the first immunoassay substrate and introducing blank solution to the second immunoassay substrate, so that the non-human antibodies against target microorganism antigen compete with human antibodies in the human sample to bind with the immobilized target microorganism antigen on the first immunoassay substrate, and human antibodies of the human sample bind with the immobilized target microorganism antigen on the second immunoassay substrate in the absence of the non-human antibodies; (d) introducing a human antibody detection reagent to each of the first and second immunoassay substrates wherein the human antibody detection reagent binds to human antibodies that remain on the substrates; and (e) generating respective first and second output signals correlative of respective amounts of human antibodies (i) binding to the human antibody detection reagent, and (ii) binding to the immobilized target microorganism antigen, on each of the respective first and second immunoassay substrates, for discriminatively detecting target microorganism antibodies in the human sample, from among antibodies of cross-reactively-related microorganisms potentially present in the human sample.

In another aspect, the disclosure relates to an immunoassay for discriminatively detecting target microorganism antibodies in a human sample, from among antibodies of cross-reactively-related microorganism(s) potentially present in the human sample, the immunoassay comprising: (a) immobilizing target microorganism antigen on each of first and second immunoassay substrates; (b) introducing corresponding amounts of the human sample to each of the first and second immunoassay substrates on which the target microorganism antigen has been immobilized; (c) providing the first immunoassay substrate with non-human antibodies against target microorganism antigen preloaded thereon, with or without introducing blank solution to the second immunoassay substrate, so that the non-human antibodies against target microorganism antigen compete with human antibodies in the human sample to bind with the immobilized target microorganism antigen on the first immunoassay substrate, and human antibodies of the human sample bind with the immobilized target microorganism antigen on the second immunoassay substrate in the absence of the non-human antibodies; (d) introducing a human antibody detection reagent to each of the first and second immunoassay substrates wherein the human antibody detection reagent binds to human antibodies that remain on the substrates; and (e) generating respective first and second output signals correlative of respective amounts of human antibodies (i) binding to the human antibody detection reagent, and (ii) binding to the immobilized target microorganism antigen, on each of the respective first and second immunoassay substrates, for discriminatively detecting target microorganism antibodies in the human sample, from among antibodies of cross-reactively-related microorganisms potentially present in the human sample.

In a further aspect, the disclosure relates to an immunoassay for discriminatively detecting target microorganism antibodies in a non-human species sample, from among antibodies of cross-reactively-related microorganism potentially present in the non-human species sample, the immunoassay comprising: (a) immobilizing target microorganism antigen on each of first and second immunoassay substrates; (b) introducing corresponding amounts of the non-human sample to each of the first and second immunoassay substrates on which the target microorganism antigen has been immobilized; (c) introducing blocking antibodies of origins other than the non-human species against target microorganism antigen to the first immunoassay substrate and introducing blank solution to the second immunoassay substrate, so that the blocking antibodies compete with the non-human species antibodies in the non-human species sample to bind with the immobilized target microorganism antigen on the first immunoassay substrate, and the non-human species antibodies of the non-human species sample bind with the immobilized target microorganism antigen on the second immunoassay substrate in the absence of the blocking antibodies; (d) introducing a non-human species antibody detection reagent to each of the first and second immunoassay substrates, wherein the non-human species antibody detection reagent binds to non-human species antibody that remain on the substrates; and (e) generating respective first and second output signals correlative of respective amounts of non-human species antibodies (i) binding to the non-human species antibody detection reagent, and (ii) binding to the immobilized target microorganism antigen, on each of the respective first and second immunoassay substrates, for discriminatively detecting target microorganism antibodies in the non-human species sample, from among antibodies of cross-reactively-related microorganism potentially present in the non-human species sample.

Another aspect of the disclosure relates to an immunoassay for discriminatively detecting target microorganism antibodies in a non-human species sample, from among antibodies of cross-reactively-related microorganism potentially present in the non-human species sample, the immunoassay comprising: (a) immobilizing target microorganism antigen on each of first and second immunoassay substrates; (b) introducing corresponding amounts of the non-human sample to each of the first and second immunoassay substrates on which the target microorganism antigen has been immobilized; (c) providing the first immunoassay substrate with blocking antibodies of origins other than the non-human species against target microorganism antigen preloaded thereon, with or without introducing the blank solution to the second immunoassay substrate, so that the blocking antibodies compete with the non-human species antibodies in the non-human species sample to bind with the immobilized target microorganism antigen on the first immunoassay substrate, and the non-human species antibodies of the non-human species sample bind with the immobilized target microorganism antigen on the second immunoassay substrate in the absence of the blocking antibodies; (d) introducing a non-human species antibody detection reagent to each of the first and second immunoassay substrates, wherein the non-human species antibody detection reagent binds to non-human species antibody that remain on the substrates; and (e) generating respective first and second output signals correlative of respective amounts of non-human species antibodies (i) binding to the non-human species antibody detection reagent, and (ii) binding to the immobilized target microorganism antigen, on each of the respective first and second immunoassay substrates, for discriminatively detecting target microorganism antibodies in the non-human species sample, from among antibodies of cross-reactively-related microorganism potentially present in the non-human species sample.

In another aspect, the disclosure relates to an immunoassay system, comprising: a single-use cartridge containing test strips constituted to perform the immunoassay as variously described herein; an integrated sample collection and processing device engageable with the single-use cartridge for delivery of sample thereto, and for operatively initiating immunoassay performance in the single-use cartridge; and a portable immunoassay test strip reader for reading immunoassay output signals from the test strips of the single-use cartridge.

Other aspects, features and embodiments of the disclosure will be more fully apparent from the ensuing description and appended claims.

DETAILED DESCRIPTION

Figure 1:
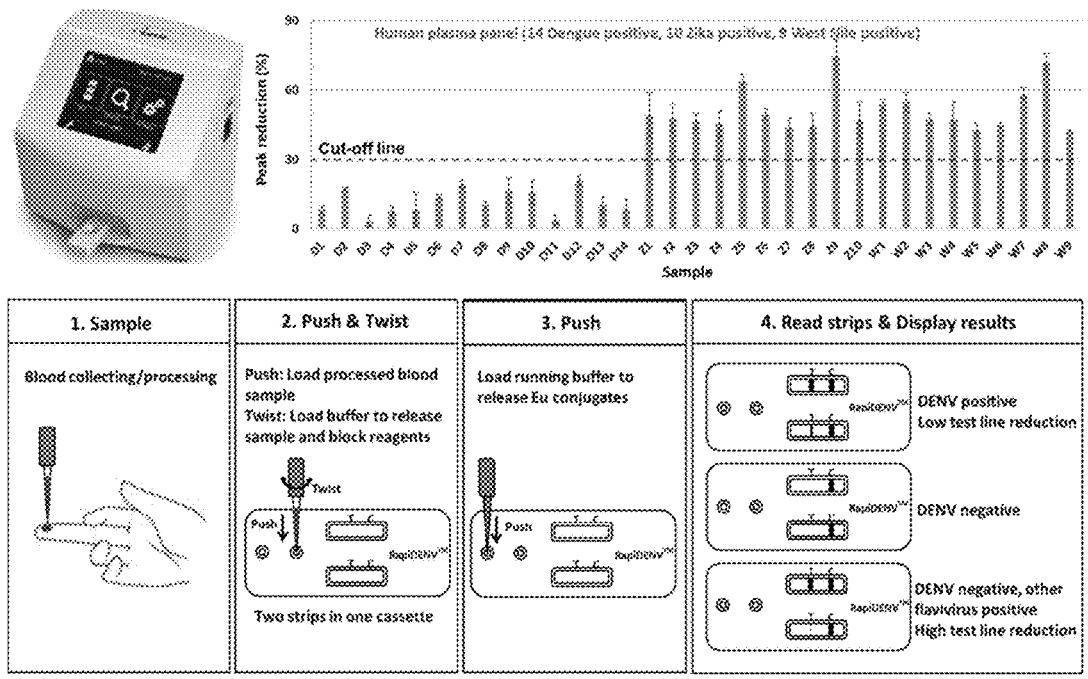
FIG. 1 is a schematic representation of an immunoassay platform and assay methodology according to one embodiment of the present disclosure, for discriminating Dengue virus from other flavivirus, with an output of the immunoassay platform reader being shown as discriminating Dengue virus infection from Zika and West Nile viral infections.

The present disclosure relates to assays and methods for discriminating closely related viruses exhibiting high levels of cross-reactivity between each other, in biological samples in which such closely related viruses may be present.

The disclosure relates in one aspect to an immunoassay for discriminatively detecting target microorganism antibodies in a human sample, from among antibodies of cross-reactively-related microorganism(s) potentially present in the human sample, the immunoassay comprising: (a) immobilizing target microorganism antigen on each of first and second immunoassay substrates; (b) introducing corresponding amounts of the human sample to each of the first and second immunoassay substrates on which the target microorganism antigen has been immobilized; (c) introducing non-human antibodies against target microorganism antigen to the first immunoassay substrate and introducing blank solution to the second immunoassay substrate, so that the non-human antibodies against target microorganism antigen compete with human antibodies in the human sample to bind with the immobilized target microorganism antigen on the first immunoassay substrate, and human antibodies of the human sample bind with the immobilized target microorganism antigen on the second immunoassay substrate in the absence of the non-human antibodies; (d) introducing a human antibody detection reagent to each of the first and second immunoassay substrates wherein the human antibody detection reagent binds to human antibodies that remain on the substrates; and (e) generating respective first and second output signals correlative of respective amounts of human antibodies (i) binding to the human antibody detection reagent, and (ii) binding to the immobilized target microorganism antigen, on each of the respective first and second immunoassay substrates, for discriminatively detecting target microorganism antibodies in the human sample, from among antibodies of cross-reactively-related microorganisms potentially present in the human sample.

As a variation of the above immunoassay, the blocking antibodies (non-human antibodies against target microorganism antigen) can be preloaded to the first immunoassay substrate at appropriate locations and the loading of blank solutions to the second immunoassay substrate may be eliminated.

Accordingly, the disclosure relates in another aspect to an immunoassay for discriminatively detecting target microorganism antibodies in a human sample, from among antibodies of cross-reactively-related microorganism(s) potentially present in the human sample, the immunoassay comprising: (a) immobilizing target microorganism antigen on each of first and second immunoassay substrates; (b) introducing corresponding amounts of the human sample to each of the first and second immunoassay substrates on which the target microorganism antigen has been immobilized; (c) providing the first immunoassay substrate with the non-human antibodies against target microorganism antigen preloaded thereon, with or without introducing blank solution to the second immunoassay substrate, so that the non-human antibodies against target microorganism antigen compete with human antibodies in the human sample to bind with the immobilized target microorganism antigen on the first immunoassay substrate, and human antibodies of the human sample bind with the immobilized target microorganism antigen on the second immunoassay substrate in the absence of the non-human antibodies; (d) introducing a human antibody detection reagent to each of the first and second immunoassay substrates wherein the human antibody detection reagent binds to human antibodies that remain on the substrates; and (e) generating respective first and second output signals correlative of respective amounts of human antibodies (i) binding to the human antibody detection reagent, and (ii) binding to the immobilized target microorganism antigen, on each of the respective first and second immunoassay substrates, for discriminatively detecting target microorganism antibodies in the human sample, from among antibodies of cross-reactively-related microorganisms potentially present in the human sample.

Such immunoassay may be conducted in any of the following implementations, with any one or more of the features of: (1) step (c) being performed before or after step (d); (2) the immunoassay being conducted to determine infection by the target microorganism of a human from whom the human sample is derived; (3) the immunoassay being conducted, in which the human antibodies are immunoglobulin G, M, A, D or E; (4) the immunoassay being conducted to determine prior infection by the target microorganism of a human from whom the human sample is derived, e.g., wherein a predetermined higher difference level between the first and second output signals contraindicating prior microorganism infection by the target microorganism, and a predetermined lower difference level between the first and second output signals indicating prior microorganism infection by the target microorganism; (5) the immunoassay being conducted to determine immunogenicity of a target microorganism vaccine, e.g., wherein a predetermined higher difference level between the first and second output signals indicates absence of immunogenicity of the target microorganism vaccine, and a predetermined lower difference level between the first and second output signals indicates immunogenicity of the target microorganism vaccine; (6) the immunoassay being conducted, wherein measurements of human antibodies against the target microorganism antigen are quantitative, semi-quantitative, or qualitative; (7) the immunoassay being conducted on a lateral flow immunoassay platform; (8) the immunoassay being conducted on an ELISA immunoassay platform; (9) immunoassay being conducted on a microparticle enzyme immunoassay platform; (10) the immunoassay being conducted, wherein the human sample comprises whole blood; (11) the immunoassay being conducted, wherein the human sample comprises serum; (12) the immunoassay being conducted, wherein the human sample comprises plasma; (13) the immunoassay being conducted, wherein the human sample comprises saliva; (14) the immunoassay being conducted, wherein the human sample comprises urine; (15) the immunoassay being conducted, wherein the human antibody detection reagent comprises optical probes, e.g., wherein the optical probes comprise gold particles, colored latex particles, enzymes, fluorescent dyes, fluorescent particles, or phosphorescent dye; (16) the immunoassay being conducted, wherein the human antibody detection reagent comprises electrochemical probes or magnetic probes; (17) the immunoassay being conducted, wherein the substrates comprise particles, plates, membranes, papers, glass beads, or microfluidic devices; (18) the immunoassay being conducted, wherein the target microorganism comprises virus; (19) the immunoassay being conducted, wherein the target virus comprises flavivirus; (20) the immunoassay being conducted, wherein the target virus comprises Dengue virus, Zika virus, West Nile virus, or Yellow Fever virus; (21) the immunoassay being conducted, wherein the target virus comprises coronavirus; (22) the immunoassay being conducted, wherein the target virus comprises herpes virus; (23) the immunoassay being conducted, wherein the target virus comprises influenza virus; (24) the immunoassay being conducted, wherein the target virus comprises hepatitis virus.

The disclosure in another aspect relates to an immunoassay for discriminatively detecting target microorganism antibodies in a non-human species sample, from among antibodies of cross-reactively-related microorganism potentially present in the non-human species sample, the immunoassay comprising: (a) immobilizing target microorganism antigen on each of first and second immunoassay substrates; (b) introducing corresponding amounts of the non-human sample to each of the first and second immunoassay substrates on which the target microorganism antigen has been immobilized; (c) introducing blocking antibodies of origins other than the non-human species against target microorganism antigen to the first immunoassay substrate and introducing blank solution to the second immunoassay substrate, so that the blocking antibodies compete with the non-human species antibodies in the non-human species sample to bind with the immobilized target microorganism antigen on the first immunoassay substrate, and the non-human species antibodies of the non-human species sample bind with the immobilized target microorganism antigen on the second immunoassay substrate in the absence of the blocking antibodies; (d) introducing a non-human species antibody detection reagent to each of the first and second immunoassay substrates, wherein the non-human species antibody detection reagent binds to non-human species antibody that remain on the substrates; and (e) generating respective first and second output signals correlative of respective amounts of non-human species antibodies (i) binding to the non-human species antibody detection reagent, and (ii) binding to the immobilized target microorganism antigen, on each of the respective first and second immunoassay substrates, for discriminatively detecting target microorganism antibodies in the non-human species sample, from among antibodies of cross-reactively-related microorganism potentially present in the non-human species sample.

As a variation of the above immunoassay, the blocking antibodies can be preloaded to the first immunoassay substrate at appropriate locations and the loading of blank solutions to the second immunoassay substrate may be eliminated.

Accordingly, the disclosure relates in a further aspect to an immunoassay for discriminatively detecting target microorganism antibodies in a non-human species sample, from among antibodies of cross-reactively-related microorganism potentially present in the non-human species sample, the immunoassay comprising: (a) immobilizing target microorganism antigen on each of first and second immunoassay substrates; (b) introducing corresponding amounts of the non-human sample to each of the first and second immunoassay substrates on which the target microorganism antigen has been immobilized; (c) providing the first immunoassay substrate with blocking antibodies of origins other than the non-human species against target microorganism antigen preloaded thereon, with or without introducing blank solution to the second immunoassay substrate, so that the blocking antibodies compete with the non-human species antibodies in the non-human species sample to bind with the immobilized target microorganism antigen on the first immunoassay substrate, and the non-human species antibodies of the non-human species sample bind with the immobilized target microorganism antigen on the second immunoassay substrate in the absence of the blocking antibodies; (d) introducing a non-human species antibody detection reagent to each of the first and second immunoassay substrates, wherein the non-human species antibody detection reagent binds to non-human species antibody that remain on the substrates; and (e) generating respective first and second output signals correlative of respective amounts of non-human species antibodies (i) binding to the non-human species antibody detection reagent, and (ii) binding to the immobilized target microorganism antigen, on each of the respective first and second immunoassay substrates, for discriminatively detecting target microorganism antibodies in the non-human species sample, from among antibodies of cross-reactively-related microorganism potentially present in the non-human species sample.

In a further aspect, the disclosure relates to an immunoassay system, comprising: a single-use cartridge containing test strips constituted to perform the immunoassay as variously described herein; an integrated sample collection and processing device engageable with the single-use cartridge for delivery of sample thereto, and for operatively initiating immunoassay performance in the single-use cartridge; and a portable immunoassay test strip reader for reading immunoassay output signals from the test strips of the single-use cartridge.

In various embodiments in which blank solution is delivered to the single-use cartridge in the performance of the assay, the integrated sample collection and processing device may correspondingly be constructed and arranged, to be engageable with the single-use cartridge for delivery of blank solution thereto, as well as delivering sample to the single-use cartridge.

The present disclosure provides an immunoassay platform and associated methodology that discriminates closely related viruses using traditional viral antigens and antibodies, in a rapid, simple, and effective assay with universal applicability to differentiate specific viral infection from all cross-reactive viruses. The immunoassay platform and methodology of the present disclosure can be utilized to track epidemiological origin, incidence, and progression of viral infections, as well as to assess the efficacy of mass vaccination efforts, and have particular advantage in the case of co-circulation of multiple closely related viruses (e.g., flaviviruses, coronaviruses).

In the assay platform and methods of the present disclosure, a target antibody is employed that has higher affinity than cross-reactive antibodies when binding with the antigen from the target virus. Specifically, an external antibody (blocking antibody) against the target virus is utilized to complete with the sample antibodies that are bound to the target antigen, leading to a signal reduction whose magnitude is indicative of (i) exposure to the target virus, as associated with and identified by a low reduction of signal, or (ii) exposure to other closely related viruses, as associated with and identified by a high reduction of signal.

The platform and methods of the present disclosure thus provide a one-step, rapid (less than 20 minutes), low cost, self-contained point-of-care (POC) diagnostic test for the measurement of antibodies against specific virus in biological samples, e.g., whole blood, serum, plasma, oral fluid, urine, spinal fluid, synovial fluid, lymphatic fluid, or other biological fluid or tissue samples. For example, in various embodiments, the platform and methodology of the present disclosure can be employed to measure IgG antibodies against Dengue virus, using lateral flow immunoassays. In such implementations, the assay significantly reduces cross-reactivity and improves diagnostic specificity, enabling differentiation of Dengue IgG from other flaviviruses and the differentiation of Dengue serotypes. In various embodiments, the platform and methodology of the present disclosure may be applied with ELISA or other immunoassays.

The present disclosure provides a generalized approach for serological discrimination of any type of target virus from closely related viruses, without the requirement of specially developed antibodies or antigens. All of the reagents utilized in the assay platform of the present disclosure, including the block antibody and the target viral antigen, can be readily obtained from commercial sources and do not require any special treatment or modification for their use. The only specific requirement for the assay platform is that the blocking antibody needs to be raised against the target viral antigen from a host species (e.g., rabbit, mouse, rat, etc.) other than human. In consequence, the assay platform of the present disclosure is of low cost and simple and effective character.

The assay platform of the present disclosure in various embodiments includes two tests that are run simultaneously with one another—a first test that is conducted with blocking antibody and a second test that is conducted without blocking antibody. Four steps are involved in this platform and methodology: (i) target viral antigen is immobilized on a membrane or plate surface in each test; (ii) clinical sample, as for example serum, plasma, or whole blood, then is added in each test; (iii) blocking antibody is next added in one test, while blank buffer solution or other suitable fluid medium without blocking antibody is added in the other test, so that the blocking antibody (non-human antibody) in such one test will compete with the sample antibodies (human antibody) to bind with the antigen, replacing a portion of the sample antibodies that are already bound to the antigen; and (iv) addition to each test of a detection reagent recognizing only the human antibodies to generate a signal in each test, so that the blocking antibody test as a result of replacement of sample antibody by the blocking antibody (non-human antibody) will exhibit a correspondingly reduced signal as compared to the signal exhibited by the test in which the blocking antibody is not present, when the target viral antigen antibody is present in the clinical sample.

Thus, signal reduction is used as a determinative parameter to differentiate target antibodies from cross-reactive antibodies in the biological sample. Specifically, based on the fact that the binding affinity and specificity of anti-viral antibodies (namely, the blocking antibody, and the target antibody in the biological sample) to the target viral antigen is higher than that of cross-reactive antibodies to the same antigen, the blocking antibody will replace cross-reactive antibodies more easily, producing higher signal reduction between the respective blocked and non-blocked tests, when the target viral antigen antibody is absent and the cross-reactive antibodies are present from the clinical sample. Contrariwise, a lower signal reduction is exhibited between the respective blocked and non-blocked tests, when the target viral antigen antibody is present from the clinical sample.

Referring now to the drawings, FIG. 1 is a schematic representation of a serological assay platform and assay methodology according to one embodiment of the present disclosure, which may be employed for example for discriminating Dengue virus from other flavivirus, with the output of the serological assay platform reader being shown in an illustrative example as discriminating Dengue virus infection from Zika and West Nile viral infections.

As illustrated in FIG. 1, the serological assay platform includes a cassette comprising a housing in which are positioned two test strips as shown. The cassette housing includes respective ports for loading blood sample and buffer into the cassette. Such ports may be configured in any suitable manner, and may be of a character that is biased to a closed position, against which the blood or buffer transfer device may be pressed to open the port to accommodate fluid transfer. The blood sample is loaded into the cassette through a first port, following which the transfer device is twisted in the port to a buffer loading position, and buffer is loaded to release the blood sample and blocking reagents. Buffer then is loaded through the second port to release beads conjugates. In this configuration, the test strips are arranged so that blocking antibody is passed to a first one of the test strips, while only buffer without any blocking antibody is passed to the other (second) one of the test strips, for lateral flow development of the respective side-by-side tests. The cassette including the developed test strips then is inserted in and read by a reader as illustratively shown in the upper left portion of FIG. 1. The reader provides quantitative results of the immunoassay, and may be of any suitable type, e.g., an Axxin AX-2X-S POC Lateral Flow Reader (Axxin Corporation, Fairfield, Victoria, Australia) as illustrated, which has dimensions of 4.8 inches×4.4 inches×4.3 inches and a weight of 1.3 pounds, enabling it to be hand-held or alternatively counter-mounted or supported.

Possible strip results are shown in the lower right portion of FIG. 1, with the top illustrated cassette showing a DENV positive output with a low test line reduction, with the middle illustrated cassette showing a DENV negative output, and the bottom illustrated cassette showing a DENV negative, other flavivirus positive output with a high test line reduction.

FIG. 1 in the upper right portion shows a graph of reader outputs in which signal peak reductions are shown for various Dengue positive samples (samples D1-D14), for various Zika positive samples (Z1-Z10), and for various West Nile positive samples (W1-W9), in a human plasma panel. The results show that the peak reduction levels associated with the Dengue positive samples are highly differentiated from those associated with the Zika positive and West Nile positive samples, such that a peak reduction value of 30% affords a cutoff line that differentiates infection by Dengue virus from viral infections by Zika virus and West Nile virus, and thereby demonstrates the quantitative serological assay results achieved by the immunoassay platform of the present disclosure.

The immunoassay platform thus may be embodied in a lateral flow test system including a point-of-care reader device, a cartridge housing two test strips, and an integrated blood collection/processing device adapted for collection of blood and delivery of blood sample and buffer to the cartridge, in which the collection/processing device is configured to carry out the lateral flow tests by simple push or push and twist movements of the device when engaged with the cartridge.

Figure 2:
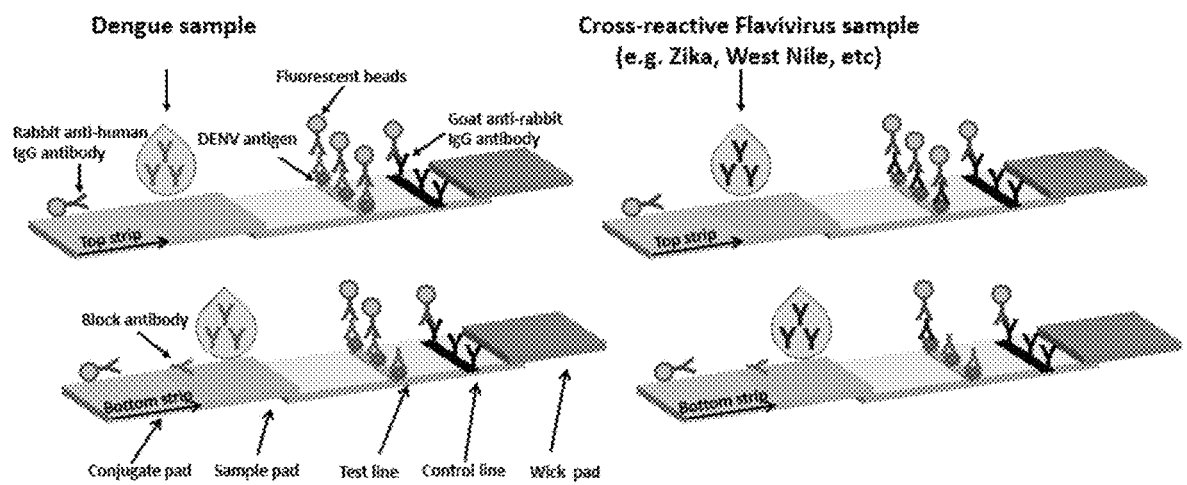
FIG. 2 is a schematic representation of a test strip layout of an immunoassay platform and assay methodology according to the present disclosure, in a specific implementation, showing antibody blocked lateral flow assay formats for high-specificity Dengue serostatus determination, using a blocking antibody mixture of four serotypes of polyclonal rabbit anti-DENV NS1 antibodies in a 1:1:1:1 ratio.

FIG. 2 is a schematic representation of a test strip layout of a serological assay platform and assay methodology according to the present disclosure, in a specific implementation, showing antibody blocked lateral flow assay formats for high-specificity Dengue serostatus determination, using a blocking antibody mixture of four serotypes of polyclonal rabbit anti-DENV NS1 antibodies in a 1:1:1:1 ratio.

As illustrated in FIG. 2, the antibody blocked assay format utilizes respective test strips (top strip and bottom strip), in which the top strip in the embodiment shown includes a conjugate pad bearing rabbit anti-human IgG antibody conjugated to fluorescent carboxylate microspheres thereon. The conjugate pad is adjacent to a sample pad to which the biological sample and buffer are introduced for permeation to the test section of the strip having Dengue antigen immobilized thereon at a test line upstream of a control line of goat anti-rabbit IgG antibody. A wick pad is located adjacent to the test section, as illustrated. In use, when a Dengue sample is introduced to the sample pad, Dengue antibodies therein will bind to the Dengue antigen at the test line of the test section of the top strip, and the rabbit anti-human IgG antibody conjugated with fluorescent beads will bind to the Dengue antibodies, and goat anti-rabbit IgG antibody at the control line will bind rabbit anti-human IgG antibody, as illustrated.

The bottom test strip in the two-strip test is correspondingly constituted with the same conjugate pad, sample pad, test section, and wick pad components, but in use additionally has non-human blocking antibody introduced to the sample pad. As mentioned, the blocking antibody will compete with human antibodies in the sample to bind with the antigen, replacing a portion of the sample antibodies that are already bound to the antigen. The rabbit anti-human IgG detection antibody will bind to the human antibodies in the sample that are bound to the DENV antigen at the test line, so that as a result of replacement of sample antibody by the non-human blocking antibody a correspondingly reduced signal is generated as compared to the signal exhibited by the test in which the blocking antibody is not present, when the target viral antigen antibody is present in the biological sample subjected to the test.

As also illustrated in FIG. 2, in the case in which the respective test strips are contacted with a biological sample containing only cross-reactive flavivirus (e.g., Zika virus, West Nile virus, etc.), and not containing Dengue virus, as illustrated in the right-hand portion of FIG. 2, the binding affinity and specificity of the non-human blocking antibody to the target viral antigen immobilized on the test section of the bottom strip will be higher than the binding affinity and specificity of the cross-reactive antibodies to the same antigen, so that the blocking antibody will replace the cross-reactive antibodies more easily, producing a higher signal reduction between the respective blocked (bottom strip) and non-blocked (top strip) tests then is achieved in the case in which the biological sample contains Dengue virus.

In this manner, the absence of the Dengue virus and presence of only other cross-reactive flaviviruses will result in a high attenuation of the detection signal (e.g., from the carboxylate fluorescent beads) that is measured between the blocked and non-blocked test strips, whereas the presence of the Dengue virus will result in a substantially reduced level of attenuation of the corresponding detection signal that is measured between the blocked and non-blocked test strips. This differential signal reduction behavior therefore enables a quantitative determination to be made of the Dengue serological status of an individual from whom the biological sample is taken. This in turn permits a rule-in/rule-out determination of the tested individual for prior Dengue virus infection.

Although the foregoing description has been directed primarily to the use of the serological assay platform and methodology of the present disclosure for detection of Dengue virus infection and serological status of human test subjects in the context of prior contemporaneous infection of such human test subjects by other, highly cross-reactive flaviviruses, it will be appreciated that the utility of the assay platform and methodology of the present disclosure is not correspondingly limited, but also extends to and encompasses applications to any other viruses and their correspondingly cross-reactive related viral species.

Thus, the serological assay platform and methodology of the present disclosure may be applied to discriminate any infectious viral agents from cross-reactively related viruses (e.g., structurally related viruses, mutants, phylogenetically related viruses, epitopically related viruses, etc.) in any viral families, including for example Adenoviridae, Anelloviridae, Arenaviridae, Astroviridae, Bornaviridae, Bunyaviridae, Caliciviridae, Coronaviridae, Filoviridae, Flaviviridae, Hepadnaviridae, Hepeviridae, Herpesviridae, Orthomyxoviridae, Papillomaviridae, Paramyxoviridae, Parvoviridae, Picobirnaviridae, Picobirna, Picornaviridae, Pneumoviridae, Polyomaviridae, Poxviridae, Reoviridae, Retroviridae, Rhabdoviridae, and Togaviridae, but the disclosure is not limited thereto.

The serological assay platform and methodology of the present disclosure can be generally utilized to discriminate any polythetic viruses or other viral cohorts displaying immunologic cross-reactivity, including any viruses that are related to one another by genetic structure, sequence homology, host range, tissue tropism, biologic reservoir, rooted transmission, epidemiology, pathogenicity, or other morphological, constitutive, or functional relational characteristics.

The advantages and features of the disclosure are further illustrated with reference to the following example, which is not to be construed as in any way limiting the scope of the disclosure but rather as illustrative of one embodiment thereof in a specific application thereof.

Example 1

Rapid Point of Care (POC) Diagnostic Test to Determine Dengue Serostatus

This example relates to a serological assay for determining previous exposure to Dengue virus, which is usefully employed as a tool in informing decision-making regarding the benefit-risk of Dengue vaccination strategies. At this time there is only one US FDA approved Dengue vaccine, Dengvaxia (CYD-TDV), with several others currently in development. However, Dengvaxia clinic trials have indicated that seronegative recipients had an increased risk of Dengue hospitalization. Therefore, a pre-vaccination screening strategy for those seeking to use CYD-TDV has become. Necessary, only permitting individuals with evidence of prior Dengue infection to be vaccinated.

In this example, an assay platform of the present disclosure of a type as shown and described with reference to FIGS. 1 and 2 herein was demonstrated using four recombinant Dengue virus Non-Structural Protein 1 (NS1) antigens: (i) Dengue virus Type 1 NS1 (amino acids 777-1131); (ii) Dengue virus Type 2 NS1 (amino acids 777-1131); (iii) Dengue virus Type 3 NS1 (amino acids 775-1129); and (iv) Dengue virus Type 4 NS1 (amino acids 776-1130), as supplied by Meridian Life Science (Memphis, Tennessee, USA).

Four related blocking antibodies were employed: (i) Polyclonal Rabbit Anti Dengue 1 NS1 IgG; (ii) Polyclonal Rabbit Anti Dengue 2 NS1 IgG; (iii) Polyclonal Rabbit Anti Dengue 3 NS1 IgG; and (iv) Polyclonal Rabbit Anti Dengue 4 NS1 IgG, as supplied by MyBioSource (San Diego, California, USA).

The assay platform enabled the differentiation of IgGs to Dengue virus from cross-reactive IgGs to other flaviviruses (e.g., Zika virus, West Nile virus).

In this example, a mixture of the four recombinant Dengue virus Non-Structural Protein 1 (NS1) antigens and the four related blocking antibodies were used to detect all four Dengue serotypes and to differentiate them from other flaviviruses. Since the binding of Dengue NS1 antigen with anti-Dengue NS1 IgGs was stronger than that with cross-reactive IgGs (other flavivirus IgGs), signal reduction from the Dengue sample was much lower than that from other flavivirus samples. When testing a non-Dengue sample, the IgG blocking reagents (i.e., rabbit anti-Dengue NS1) preferentially replaced the cross-reactive IgGs from non-Dengue samples and bound to Dengue NS1 immobilized on the membrane; the signal generating reagent could not recognize these blocking IgGs originated from rabbit leading to significantly reduced signals. However, for a Dengue positive sample, the blocking reagent competed with the anti-Dengue IgGs that were already bound to the Dengue NS1 antigens, leading to slightly reduced test line signal. The successful differentiation of Dengue from other flavivirus was demonstrated by achieving 100% sensitivity and 100% specificity of the assay based on testing of a total of 38 commercial flavivirus samples (14 Dengue samples, 10 Zika samples, 9 West Nile samples, and 5 negative samples), with the results shown in the signal attenuation graph of FIG. 1 herein.

The results of this example demonstrate the use and effectiveness of the serological assay platform and method of the present disclosure for measurement of Dengue IgG antibodies directly from blood by application of a fluorescent lateral flow immunoassay. The assay system employed in this example was of a simple character, employing a single-use lateral flow cartridge with an integrated blood collection and processing device, and a portable lateral flow immunoassay test strip reader, as a system for one-step, rapid (<20 minutes), low cost point-of-care determination of Dengue virus infection.

While the disclosure has been set forth herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the disclosure as hereinafter claimed is intended to be broadly construed and interpreted, as including all such variations, modifications and alternative embodiments, within its spirit and scope.

What is claimed is:

1. An immunoassay for discriminating human antibodies specific for a target virus from human cross-reacting antibodies to related viruses in a single sample, wherein the target virus comprises a flavivirus, a coronavirus, a herpes virus, an influenza virus, or a hepatitis virus, the immunoassay comprising:
   (a) immobilizing target virus antigens on each of a first immunoassay substrate and a second immunoassay substrate,
   (b) introducing corresponding amounts of the sample to each of the first immunoassay substrate and the second immunoassay substrate on which the target virus antigens have been immobilized;
   (c) (i) introducing non-human antibodies against the target virus antigens to the first immunoassay substrate and introducing a blank solution to the second immunoassay substrate,
   or alternatively,
      (ii) providing the first immunoassay substrate with the non-human antibodies preloaded thereon, with or without introducing a blank solution to the second immunoassay substrate,
      so that the non-human antibodies against the target virus antigens compete with human antibodies in the sample to bind with the immobilized target virus antigens on the first immunoassay substrate, and human antibodies of the sample bind with the immobilized target virus antigens on the second immunoassay substrate in the absence of the non-human antibodies;
   (d) introducing a human antibody detection reagent to each of the first and second immunoassay substrates wherein the human antibody detection reagent binds to human antibodies that remain on the first immunoassay substrate and the second immunoassay substrate; and
   (e) generating a first output signal correlative of a first amount of human antibodies bound with target virus antigens immobilized on the first immunoassay substrate and generating a second output signal correlative of a second amount of human antibodies bound with target virus antigens immobilized on the second immunoassay substrate,
      wherein a predetermined higher difference level between the first and second output signals contraindicate the presence of antibodies to target virus, and a predetermined lower difference level between the first and second output signals indicate the presence of antibodies to the target virus.

2. The immunoassay of claim 1, wherein the immunoassay is conducted to determine infection by the target virus of a human from whom the sample is derived.

3. The immunoassay of claim 1, wherein the human antibodies are immunoglobulin G, M, A, D or E.

4. The immunoassay of claim 1, wherein the immunoassay is conducted to determine prior infection by the target virus of a human from whom the sample is derived.

5. The immunoassay of claim 1, wherein the immunoassay is conducted to determine immunogenicity of a target virus vaccine.

6. The immunoassay of claim 1, wherein measurements of human antibodies against the target virus antigen are quantitative, semi-quantitative, or qualitative.

7. The immunoassay of claim 1, wherein the immunoassay is conducted on a lateral flow immunoassay platform.

8. The immunoassay of claim 1, wherein the immunoassay is conducted on an ELISA immunoassay platform.

9. The immunoassay of claim 1, wherein the immunoassay is conducted on a microparticle enzyme immunoassay platform.

10. The immunoassay of claim 1, wherein the sample comprises whole blood.

11. The immunoassay of claim 1, wherein the sample comprises serum.

12. The immunoassay of claim 1, wherein the sample comprises plasma.

13. The immunoassay of claim 1, wherein the sample comprises saliva.

14. The immunoassay of claim 1, wherein the sample comprises urine.

15. The immunoassay of claim 1, wherein the human antibody detection reagent comprises optical probes.

16. The immunoassay of claim 13, wherein the optical probes comprise gold particles, colored latex particles, enzymes, fluorescent dyes, fluorescent particles, or phosphorescent dye.

17. The immunoassay of claim 1, wherein the human antibody detection reagent comprises electrochemical probes or magnetic probes.

18. The immunoassay of claim 1, wherein the substrates comprise particles, plates, membranes, papers, glass beads, or microfluidic devices.

19. The immunoassay of claim 1, wherein the flavivirus comprises Dengue virus, Zika virus, West Nile virus, or Yellow Fever virus.

20. An immunoassay for discriminating non-human antibodies specific for a target virus from non-human cross-reacting antibodies to related viruses in a single sample, wherein the target virus comprises a flavivirus, a coronavirus, a herpes virus, an influenza virus, or a hepatitis virus, the immunoassay comprising:
   (a) immobilizing target virus antigens on each of a first immunoassay substrate and a second immunoassay substrate,
   (b) introducing the non-human sample comprising antibodies to each of the first immunoassay substrate and the second immunoassay substrate on which the target virus antigens have been immobilized;
   (c) (i) introducing blocking antibodies of origins other than the non-human species against target virus antigens to the first immunoassay substrate and introducing a blank solution to the second immunoassay substrate, or alternatively,
   (ii) providing the first immunoassay substrate with blocking antibodies preloaded thereon, with or without introducing a blank solution to the second immunoassay substrate,
   so that the blocking antibodies compete with the non-human species antibodies in the non-human species sample to bind with the immobilized target virus antigens on the first immunoassay substrate, and the non-human species antibodies of the non-human species sample bind with the immobilized target virus antigens on the second immunoassay substrate in the absence of the blocking antibodies;
   (d) introducing a non-human species antibody detection reagent to each of the first and second immunoassay substrates, wherein the non-human species antibody detection reagent binds to non-human species antibody that remain on the first immune assay substrate and the second immunoassay substrate; and
   (e) generating a first output signal correlative of a first amount of non-human antibodies bound with target virus antigens immobilized on the first immunoassay and generating a second output signal correlative of a second amount of non-human antibodies bound with target virus antigens immobilized on the second immunoassay,
   wherein a predetermined higher difference level between the first and second output signals contraindicates the presence of non-human antibodies to target virus, and a predetermined lower difference level between the first and second output signals indicates the presence of non-human antibodies to the target virus.

* * * * *